United States Patent [19]

Sabbota et al.

[11] 4,375,811

[45] Mar. 8, 1983

[54] SURGICAL VENTILATING APPARATUS

[75] Inventors: Howard I. Sabbota, Southfield; Marvin H. Weintraub, West Bloomfield, both of Mich.

[73] Assignee: Future Teck, Southfield, Mich.

[21] Appl. No.: 237,743

[22] Filed: Feb. 24, 1981

[51] Int. Cl.³ .................................... A61M 25/00
[52] U.S. Cl. .................................. 604/97; 604/35; 604/77
[58] Field of Search ............. 128/207.14, 207.15, 128/348, 349 R, 4, 10; 1/207.16, 207.17, 347, 349 B, 349 BV, 200.26, 239

[56] References Cited

U.S. PATENT DOCUMENTS

| | | | |
|---|---|---|---|
| 3,225,767 | 12/1965 | Smith | 128/200.26 |
| 3,400,714 | 9/1968 | Sheridan | 128/239 |
| 3,460,541 | 8/1969 | Doherty | 128/207.15 |
| 3,529,633 | 9/1970 | Vaillancourt | 128/349 R |
| 3,556,103 | 1/1971 | Calhoun et al. | 128/347 |
| 3,788,326 | 1/1974 | Jacobs | 128/207.15 |
| 3,854,484 | 12/1974 | Jackson | 128/207.15 |
| 3,964,488 | 6/1976 | Ring et al. | 128/351 |
| 3,989,571 | 11/1976 | Harautuneian | 128/207.15 |
| 4,050,466 | 9/1977 | Koerbacher | 128/351 |
| 4,155,356 | 5/1979 | Venegas | 128/207.14 |
| 4,248,221 | 2/1981 | Winnard | 128/207.15 |
| 4,282,875 | 8/1981 | Serbinenko et al. | 128/349 B |

OTHER PUBLICATIONS

Attia et al., "Trantracheal Ventilation", JAMA, Dec. 15, 1975, vol. 234, No. 11, pp. 1152-1153.

*Primary Examiner*—Henry J. Recla
*Attorney, Agent, or Firm*—Basile, Weintraub & Hanlon

[57] ABSTRACT

Surgical ventilating apparatus for use in laser surgical techniques. The surgical ventilating apparatus comprises a hollow, flexible, tubular body formed of a heat-resistant material, such as an oxide of a metal, an expanded or foamed silica or quartz, and the like. The tubular body is formed so as to resist vibration when disposed within the trachea of a patient caused by the high velocity of air flowing therethrough. In one embodiment, at least one rod-like member is embedded within the tubular body to provide a degree of rigidity thereto. In another embodiment, the end of the tubular body is flared to reduce vibration of the tubular body. A connector adapted to be connected to one end of the tubular body enables the tubular body to be connected to ventilating equipment for controlling the respiration of the patient during surgery.

8 Claims, 5 Drawing Figures

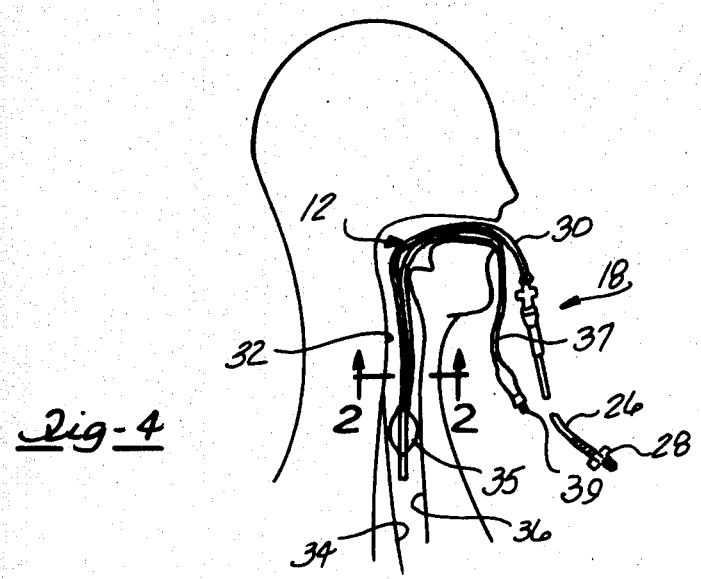
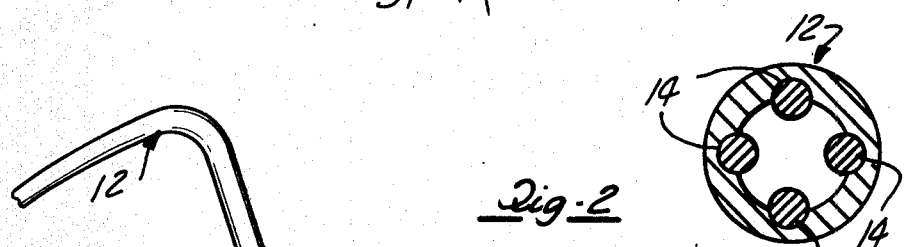
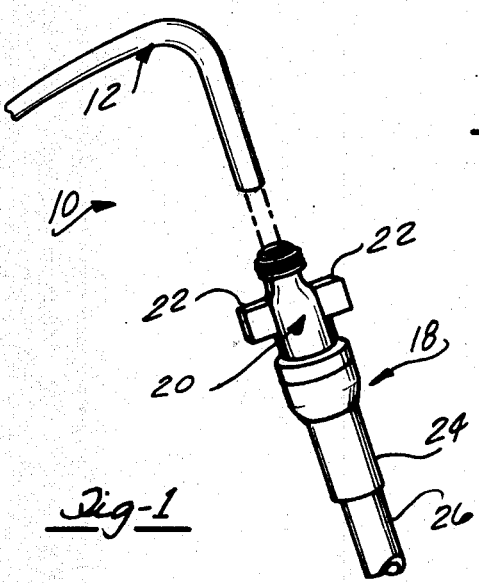
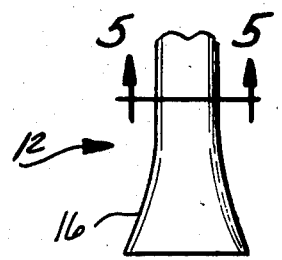
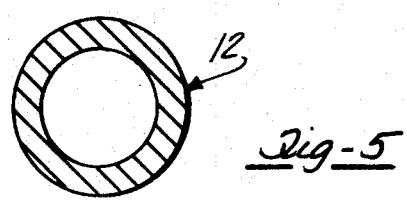

SURGICAL VENTILATING APPARATUS

BACKGROUND OF THE INVENTION

1. Field of the Invention:

This invention relates, in general, to surgical apparatus and, more specifically, to surgical ventilating apparatus, such as tracheal tubes.

2. Description of the Prior Art:

A commonly used device in the medical field is a tracheal tube which is particularly useful during surgical procedures for maintaining control over the patient's breathing. Commonly, tracheal tubes are manufactured from resilient type material which automatically conform in shape and curvature to the body requirements.

As is well known, present day tracheal tubes are inserted through the patient's mouth and beyond, into the lower portions of the trachea. The outer end of the tube is connected to suitable medical apparatus, such as a suction device for aspirating the trachea, a source of anesthesia or the like.

Although such tracheal tubes function effectively to permit controlled respiration of the patient, recent surgical advances, such as microlaryngeal operations utilizing lasers, have posed problems for their continued effective use. In such laser surgical techniques, the heat generated by the high intensity laser beams quickly perforates or severs conventionally constructed tracheal tubes, rendering them useless and posing serious danger to the patient.

Efforts to construct tracheal tubes of material having a higher heat resistivity have met with little success. Tubes covered with aluminum foil tape and/or muslin wrappings present the danger of small portions becoming dislodged during surgery as well as being relatively complex and cumbersome to construct.

Further, most material having the necessary high heat resistivity is somewhat rigid which retards its safe use during insertion and removal from the patient's trachea.

It has been found in the practice of laser-based laryngoscopy, microlaryngoscopy or bronchoscopy that the high velocity of the air flowing through a tracheal tube from a jet injector during such operations causes excessive vibration of the free end of the tube. This not only poses a danger to the patient, but also causes the tracheal tube to pass through the laser beam resulting in damage to the tube.

Thus, it would be desirable to provide a surgical ventilating apparatus which overcomes the problems of the prior art ventilating apparatus when used in surgical techniques using lasers, as well as bronchoscopy, or endoscopy techniques. It would also be desirable to provide a surgical ventilating apparatus which minimizes the danger to the patient during its use. It would also be desirable to provide a surgical ventilating apparatus which is simple to construct and which resists the heat of high intensity laser beams. Finally, it would be desirable to provide a surgical ventilating apparatus which is flexible so as to conform in shape and curvature to the patient's trachea.

SUMMARY OF THE INVENTION

There is disclosed herein a new and improved surgical ventilating apparatus useful in surgical procedures which must provide greater access to the tracheal area. The present invention is particularly useful with surgical techniques utilizing high intensity lasers, bronchoscopies or endoscopies. The surgical ventilating apparatus of this invention comprises a hollow, flexible, tubular body formed of a heat-resistant material. Preferably, the tubular body is formed of an oxide, such as an aluminum oxide or a blend thereof with magnesium oxide, silver oxide, and the like. Other useful materials include expanded or foamed silica, perlite, quartz, copper and oxides of copper.

Means are provided for preventing vibration of the free end of the tubular body caused by the high velocity of air flowing therethrough during an operation. In one embodiment, at least one and, preferably, a plurality of rod-like members are provided within the interior of the tubular body. The rod-like members extend along the length of the tubular body and are joined thereto to provide a degree of rigidity that resists vibration. In another embodiment, the free end of a non-reinforced tubular body is flared in an enlarged conical configuration to reduce the turbulence of air flowing out of the tubular body and thereby prevent vibration of the free end of the tubular body.

Suitable connector means adapted to be secured to one end of the tubular body enable the surgical ventilating apparatus of this invention to be connected to conventional ventilating equipment for controlling the respiration of the patient.

The new and improved surgical ventilating apparatus of this invention is ideally suited for use with newly developed surgical techniques utilizing high intensity laser beams for cutting or cauterizing. The tubular body is flexible so as to conform in shape and curvature to the body requirements of the patient's trachea. Further, the heat resistive tubular body resists the high intensity heat generated by the laser which heretofore frequently perforates or severs conventionally formed tracheal tubes. The tubular body is constructed so as to prevent vibration of its free end during an operation caused by the high velocity of air flowing therethrough. Finally, the surgical ventilating apparatus of this invention is simple to construct which further enhances its use in those surgical techniques requiring greater access to the tracheal area.

BRIEF DESCRIPTION OF THE DRAWING

Various features, advantages and other uses of this invention will become more apparent by referring to the following detailed description and drawing in which:

FIG. 1 is a perspective view of a surgical ventilating apparatus constructed in accordance with the teachings of this invention;

FIG. 2 is a cross sectional view, generally taken along line 2—2 in FIG. 4, showing one embodiment of the surgical ventilating apparatus of this invention;

FIG. 3 is a partial view of another embodiment of the surgical ventilating apparatus;

FIG. 4 is a schematic view of the surgical ventilating apparatus of the present invention inserted into the trachea of the patient; and FIG. 5 is a cross sectional view generally taken along line 5—5 in FIG. 3.

DESCRIPTION OF THE PREFERRED EMBODIMENTS

Throughout the following description and drawing, identical reference numbers are used to refer to the same component shown in multiple figures of the drawing.

Referring now to the drawing, and to FIG. 1 in particular, there is illustrated a surgical ventilating apparatus 10 constructed in accordance with the teachings of the present invention. The surgical ventilating apparatus 10 is constructed so as to be suitable for use with surgical techniques utilizing high intensity laser beams.

The surgical ventilating apparatus 10 of this invention comprises an elongated tubular body 12. The tubular body 12 may be of any suitable length, such as 11 to 12 inches, and may further be constructed of varying diameters so as to be utilized in many different surgical applications and with different sized patients, from babies to adults.

As shown in FIG. 2, the tubular body 12 is of substantially circular cross section and forms a hollow conduit throughout its length. The tubular body 12 is formed of a material having high heat resistivity so as to resist deterioration or perforation under the bombardment of high intensity laser beams during surgery. Preferably, the tubular body 12 is formed of any non-toxic material which can withstand the high temperature generated by intense laser beams. Particularly useful are certain oxides which can be formed into a hollow conduit. Suitable oxides include, for example, aluminum oxide, magnesium oxide, as well as blends thereof, silver oxide, zinc oxide, titanium oxide and the like. Other useful materials include expanded or foamed silica, foamed quartz, expanded perlite, copper and oxides of copper. Depending on the temperature, aluminates may be used. While providing the requisite degree of heat resistivity, such materials are also flexible so as to conform to the shape and curvature of the trachea of a patient. In practicing the present invention, the tubular body is formed, preferably, of either aluminum oxide or a blend thereof with magnesium oxide, such as that sold under the name Fiberflex.

Referring now to FIGS. 1 and 4, the surgical ventilating apparatus 10 of this invention includes means, denoted in general at reference number 18, for connecting the surgical ventilating apparatus 10 to conventional ventilating equipment, such as a suction device for aspirating the trachea or a source of anesthesia, not shown. The connecting means 18 includes a suitably formed hollow connector 20 having a plurality of threads extending from opposed sides thereof. The connector 20 includes a pair of flanges 22 which form a convenient means for screwing the connector 20 into one end of the tubular body 12. The opposite end of the connector 20 is threadingly secured to a sleeve 24 which sealingly mates a hollow conduit 26, such as plastic tubing, to the connector 20. As shown in FIG. 4, the opposite end of the conduit 26 is provided with a suitably formed connector 28 so as to enable the conduit 26 to be joined to the selected ventilating equipment.

In use, the connector 20 is threadingly secured to one end of the tubular body 12. The conduit 26 is then joined to the opposite end of the connector 20, with the opposed end of the conduit 26 joined to the ventilating equipment by means of the connector 28.

As shown in FIG. 4, the first portion of the tubular body 12 is inserted through the mouth 30 and larnyx 32 of a patient. The tubular body 12 is inserted into the trachea 34 of the patient until the end thereof is properly positioned in the vestibular portion 36 of the trachea 34 of the patient. Preferably, the surgical ventilating apparatus 10 is formed with an inflatable low pressure cuff 35 which is disposed around and integrally joined to the lower end of the tubular body 12. A flexible conduit 37 extends between the cuff 35 and an external self-sealing inflation valve 39. The valve 39 is adapted to receive a syringe for injecting air into the cuff 35 to inflate the cuff 35 and completely seal the trachea 34.

In this manner, controlled respiration of the patient during surgery can be easily obtained. In addition, surgical equipment incorporating high intensity lasers may then be inserted and directed into the trachea 34 of the patient without the danger of the heat generated by the high intensity laser beams perforating or severing the tubular body 12 and posing a danger to the patient. It should be noted with respect hereto that the connector assembly hereof is useful with any conventional anesthesia breathing circuit, such as a Sanders ventilator or the like.

It has been found in practice, that the high velocity of the air flowing through conventionally formed trachea tubes causes vibration of the free end of such tubes within the trachea of the patient. This not only poses a danger to the patient, but also presents additional problems when trachea tubes are used with high intensity lasers. The vibration and movement of the free end of such tubes could intercept the laser beam and thereby result in damage to the trachea tube.

In order to overcome such problems, the surgical ventilating apparatus 10 of the present invention includes means for preventing vibration of the free end of the tubular body 12. In one embodiment, as shown in FIG. 2, the means for preventing vibration of the tubular body 12 comprises at least one rod-like member 14 which is disposed within the tubular body 12 and joined thereto. The rod-like member 14 is preferably formed of a metallic material to provide a degree of rigidity to the tubular body 12 so as to prevent vibration of the free end of the body 12 caused by the velocity of air flow therethrough. As shown in FIG. 2, a plurality of rod-like members 14 are provided within the tubular body 12 and joined thereto in a conventional manner, such as by integrally molding the rod-like members 14 to the tubular body 12 during its construction.

Referring now to FIGS. 3 and 5, there is shown another embodiment of the means for preventing vibration of the free end of the tubular body 12. In this embodiment, the free end of the tubular body 12 is formed with an enlarged conical shape 16. This enlarged area at the free end of the tubular body 12 reduces the turbulence caused by air flow therethrough and prevents the free end of the tubular body 12 from vibrating during use. Since the flared end 16 substantially eliminates vibration of the free end of the tubular body 12, the reinforcing members 14 may be eliminated such that the tubular body 12 retains its hollow, circular cross section as shown in FIG. 5.

Thus, there has been described herein a new and improved surgical ventilating apparatus that is suitable for use with new surgical techniques utilizing high intensity lasers, bronchoscopies, endoscopies and the like which require greater access to the tracheal area. The surgical ventilating apparatus comprises a tubular body adapted to be inserted into the trachea of the patient which is constructed of a heat-resistive material. The heat-resistive material resists perforation despite bombardment of the heat generated by the high intensity laser during surgical procedures. In this manner, respiration of the patient during surgery is continually controlled with little additional danger posed to the patient by the use of the high intensity laser.

What is claimed is:

1. Surgical ventilating apparatus comprising:
    a hollow, flexible, tubular body formed of a material which is not perforated during laser surgery selected from the group consisting of copper, an oxide and blends thereof, silver oxide, zinc oxide, titanium oxide, expanded silica, expanded perlite, foamed quartz, an aluminate or mixtures thereof;
    said tubular body being adapted to be connected at one end to patient ventilating equipment and to have the other free end disposed within the trachea of a patient;
    said tubular body including means for preventing vibration of said free end of said tubular body due to air flow therethrough.

2. The surgical ventilating apparatus of claim 1 wherein the means for preventing vibration of the tubular body comprises:
    at least one metallic rod-like member disposed within said tubular body and joined thereto.

3. The surgical ventilating apparatus of claim 1 wherein the means for preventing vibration of the tubular body comprises:
    the free end of said tubular body having an enlarged conical configuration.

4. The surgical apparatus of claim 1 wherein the tubular body is formed of aluminum oxide, copper or an oxide of copper.

5. The surgical apparatus of claim 1 wherein the tubular body is formed of a blend of aluminum oxide and magnesium oxide.

6. Surgical ventilating apparatus comprising:
    a hollow, flexible, tubular body formed from a blend of aluminum oxide and magnesium;
    said tubular body being adapted to be connected at one end to patient ventilating equipment and to have the other free end disposed within the trachea of a patient;
    said tubular body including means for preventing vibration of said free end of said tubular body due to air flow therethrough.

7. The surgical ventilating apparatus of claim 6 wherein the means for preventing vibration of the tubular body comprises:
    at least one metallic rod-like memaw disposed within said tubular body and joined thereto.

8. The surgical ventilating apparatus of claim 6 wherein the means for preventing vibration of the tubular body comprises:
    the free end of said tubular body having an enlarged conical configuration.

* * * * *